United States Patent [19]
Bailey et al.

[11] Patent Number: 6,007,504
[45] Date of Patent: Dec. 28, 1999

[54] MOULDABLE PRODUCT

[75] Inventors: Stuart Graham Bailey; Alaster McDonach, both of Glasgow, United Kingdom

[73] Assignee: University of Strathclyde, Glasgow, United Kingdom

[21] Appl. No.: 08/981,705

[22] PCT Filed: Jul. 12, 1996

[86] PCT No.: PCT/GB96/01664

§ 371 Date: Jan. 6, 1998

§ 102(e) Date: Jan. 6, 1998

[87] PCT Pub. No.: WO97/02843

PCT Pub. Date: Jan. 30, 1997

[30]     Foreign Application Priority Data

Jul. 12, 1995 [GB] United Kingdom .................. 9514252

[51] Int. Cl.⁶ ..................................................... A61F 5/00
[52] U.S. Cl. ........................................ 602/6; 602/8; 602/9
[58] Field of Search ........................................ 602/6, 8, 9

[56]         References Cited

U.S. PATENT DOCUMENTS 4,077,390  3/1978  Stanley et al. .

FOREIGN PATENT DOCUMENTS 0 352 095  1/1990  European Pat. Off. .
0 485 835  5/1992  European Pat. Off. .

*Primary Examiner*—Jerome W. Donnelly
*Assistant Examiner*—Kelvin Hart
*Attorney, Agent, or Firm*—Alston & Bird LLP

[57]         ABSTRACT

A mouldable product such as a pad which can be selectively transformed between pliable and rigid states is formed of a sealed plastic container which houses a metastable compound such as sodium acetate tri-hydrate, a trigger device for initiating the nucleating process in the compound to render it rigid, and a reinforcing open micro-porous material. The material may be fibrous, e.g., cotton, and stabilizes the product in its rigid state for a comparatively long time.

8 Claims, 1 Drawing Sheet

MOULDABLE PRODUCT

This invention relates to mouldable products.

Mouldable materials based on using metastable hydrated salts have been described previously (EP 485,835 and EP 521,333) for making plaster bandages for supporting broken limbs and the like. These metastable hydrated salts allow a bandage to be formed which is mouldable while the salt is liquid, and becomes rigid when the salt solidifies. Although there has been some interest in these salts, the ability to use the solid salt within other useful products is limited by the poor structural properties of the crystallite. Simple hand pressure and manipulation is enough to damage the shape of the solid form. Failure is by crystal fracture and by crystal/crystal separation and movement.

It is an object of the present invention to mitigate this disadvantage and to provide a mouldable product comprising a metastable compound, which is of enhanced structural strength in its solid state.

The present invention provides a mouldable product which is conformable in that it can be selectively converted from a mouldable state to a reinforced solid state and which in its mouldable state can be shaped or conformed to any desired configuration, said product comprising a sealed container made of permanently flexible material and a fill composition within said container, said composition comprising a reinforcing open micro-porous material which is liquid absorbing and a metastable compound dispersed through said micro-porous material.

The micro-porous material is liquid-absorbing, and provides mechanical reinforcement for the metastable compound when in its solid state which results in structural integrity of the rigid moulded or conformed product over a comparatively long period of time (e.g. 6 weeks). The micro-porous material may be a fibrous material, a hydrogel material or alternatively a particulate material. The micro-porous material is sufficiently fine to assist the metastable compound in a liquid/gel like (mouldable) state to form a micro-connected matrix structure and the liquid-absorbing nature of the material enables the crystals of the metastable compound when in a solid (rigid) state to bind to the micro-porous material.

Preferably, the mouldable product can be converted from a mouldable state to a reinforced state in a reversible manner i.e. it is reconformable.

A phase transformation in the product (i.e. mouldable to rigid) occurs during the conversion from the mouldable state to the reinforced solid state. This transformation is effected by a trigger mechanism. This mechanism once triggered results in a rapid conversion of the product from a mouldable state to the solid state.

This trigger mechanism may simply be a consequence of manipulating the product around an article of choice, such as a broken limb. The actual act of moulding the product triggers the mechanism and the product transforms from a mouldable product to a rigid solid product. Alternatively, additional devices may effect the change in state. Such additional devices may include devices for heating or cooling the product. The heating or cooling of the product thus acts as a trigger. Applying an electrical current as a trigger mechanism, through the product, is another alternative. A flexible metal strip with micro slits cut into the surface of the strip may be used to provide the trigger. Flexing of the strip provides the trigger for initiating phase transformation of the product. It is thought that growth of the crack tip of the micro slit upon flexing triggers the phase transformation.

It is the metastable compound which is transformed from a liquid to a solid state which results in the product being converted from a mouldable product to a rigid solid product. The metastable compound may be convertible between its solid and liquid states by trigger mechanisms (commonly termed nucleating processes) which may be similar to those previously described in the art (e.g. Anonymous, Vol. I No. 1. 1986, Hashimoto, T. and Kotoni, Y. "A nucleating device with Special Electrodes for some Supercooled Hydrates". Japan Association of Crystal Growth 9, 31 (1982) and U.S. Pat. Nos. 4,587,950 and 4,077,390). It is thought that the trigger mechanisms locally reduce the thermodynamic barrier to the water molecules rearranging themselves around the anhydrous salt components, resulting in the formulation of a nucleating particle and the commencement of the phase transformation.

The metastable compound is preferably a hydrated salt of sodium or calcium, such as sodium acetate tri-hydrate [$NaHC_3OO.3H_2O$] which has a melting temperature of 58° C.; or sodium sulphate pentahydrate [$NaSO_4.5H_2O$] which has a melting temperature of 32.8° C.; calcium nitrate hydrate [$Ca(NO_3)_2.4H_2O$] which has a melting temperature of 44° C. Optionally other hydrated salts such as Sodium bromide dihydrate ($NaBr. 2H_2O$) may be added to the hydrated salt to form a mixture. This may have an effect on the properties of the hydrated salts, and in particular on supercooling properties of the hydrated salts.

These salts have a number of useful properties that make them attractive for heat storage applications. Firstly, the hydrated salts have large latent heat of fusion/crystallisation and their melting temperatures are in the range 20–90° C. which overlaps with the operating temperature of terrestrial solar energy systems. Also, there is the possibility of using the supercooling behaviour to provide temporary and portable heat storage systems which can be charged and discharged by controlling the nucleation conditions of the material.

A preferred trigger/nucleating mechanism utilises the properties of supercooling behaviour, which is a common feature of hydrated salts such as Sodium Acetate Trihydrate. In the supercooled state, the hydrated salt will remain in the liquid phase at a temperature below its freezing temperature. During phase changes such as freezing/melting, nucleation is necessary to allow crystallisation. If there are no nucleation sites then the material will form a superheated solution, in the case of a liquid heated above its boiling point, or a supercooled liquid in the case of cooling below its freezing temperature. The stability of this state depends on the thermodynamic changes associated with crystallisation or dissassociation. In the particular case of the hydrated salt, the chemical potential of the water must increase as the water molecules rearrange themselves into the surrounding of the solid hydrate. This results from the fact that the chemical potential of the water in the crystalline state is higher than that in the supercooled melt. The difference in the chemical potential may be considered as a rough measure of the barrier to nucleation. In the case of hydrated salts the height of this barrier is of a level to have a very noticeable effect on its behaviour.

For example if a metastable salt such as Sodium acetate trihydrate is supercooled, it will remain liquid until it encounters a nucleating particle which provides a surface or point where the chemical equilibrium conditions are modified to the extent that the potential barrier to the rearrangement of the water molecules is removed. Once the nucleating particle is encountered, the supercooled liquid will commence the process of solidification. The formation of the solid phase proceeds throughout the body of the material since the crystal surface itself acts as a nucleating surface for the remaining supercooled liquid in contact with this interface.

In a first embodiment, the micro-porous material may be a fibrous material formed of cotton wool or jute or hollowfill fibres such as DACRON™-Holofil or polyacrylonitrile hollow fibres. Hollowfill fibres with core diameters of 30–80 μm are typical. However, fibres with core diameters up to 250 μm can be obtained. Without wishing to be bound by any particular theory, it is believed that the metastable compound is drawn into the hollow core of the fibre, which influences the mechanism and metastable behaviour of the composition. The fibres may also function to entrap air within the composition, giving reinforcement while reducing composition density.

In another embodiment the micro-porous material may be formed from a hydrogel. Many hydrogels have been described previously and particularly preferred hydrogels include polyurethane based hydrogels, polyethylene oxide hydrogels, cellulose based hydrogels and polyacrylic acid hydrogels. The hydrogels have the effect of reducing the stability of the metastable state as well as influencing the mechanical properties of the liquid state. Fibrous or particulate hydrogels may be used, depending on any given application.

In a further embodiment the micro-porous material may be in the form of a particulate material, resulting in a particulate inclusion composition being formed with the metastable compound. Such particulate materials include glass or nylon hollow spheres (e.g. micro-glass spheres supplied by 3M under the name BALOTINI™) and "bubble-pack" plastics. The particulate material also influences the properties of the composition and provides for air entrapment, which reduces the density and stiffness if the solid state.

The sealed container may be made of a woven fabric so as to be permanently flexible or may be made of plastic film material. To provide the required seal it requires to be non-porous in relation to the metastable compound when in its liquid state. The container may be pre-shaped to enable the mouldable product with the metastable compound in its liquid state to fit conveniently into a receiving article. By way of example the container may be pre-shaped to form a shoe or boot insert (e.g. a ski boot liner) or an interior lining for a motor sport crash helmet, or a splint/support for accident and emergency use.

Embodiments of the present invention will now be described by way of example, with reference to the accompanying drawings in which.

Figure 1:
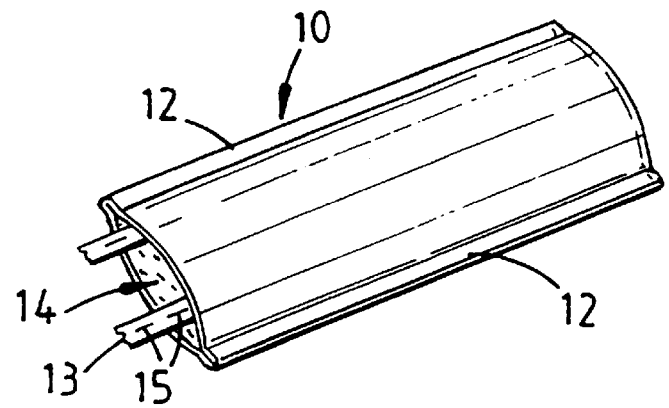
FIG. 1 is a partial cutaway perspective view of a mouldable product of the present invention.

FIG. 1 shows a mouldable product according to the present invention. The mouldable product has been formed into a cushion or pad 10 which may be moulded around a particular object, for instance, a broken leg. The pad has been formed of a fill composition 14, flexible metal strips 13 containing micro slits 15 and an outer flexible plastics covering 12 which seals in the fill composition 14 and metal strips 13 forms the pad 10.

Figure 2A:
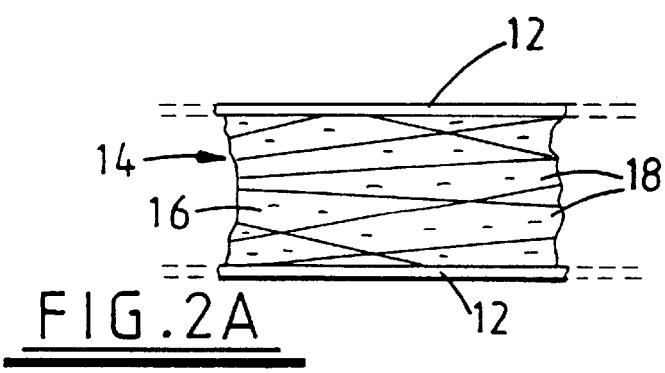
FIGS. 2A, 2B and 2C are schematical cross-sectional views of various embodiments of the mouldable product shown in FIG. 1.
Figure 2B:
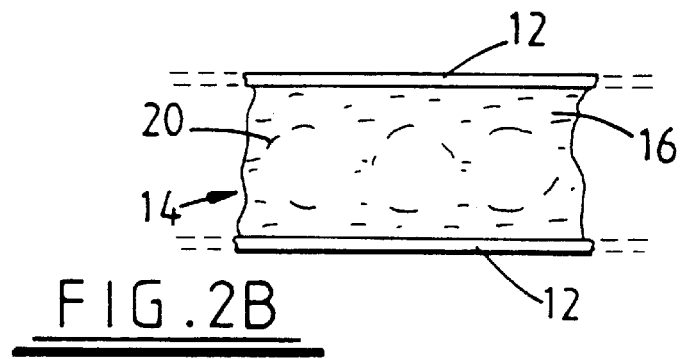
Figure 2C:
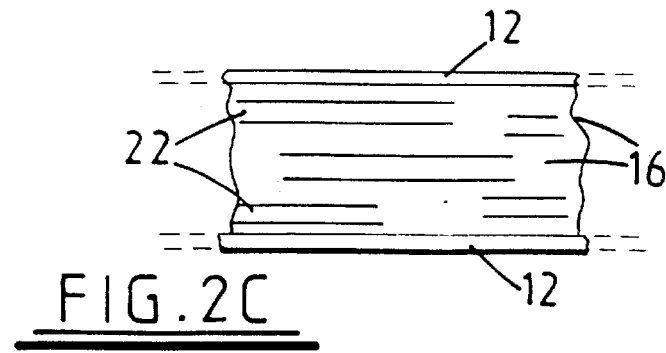

The fill composition has two distinct phases, a mouldable phase and a rigid. The fill composition 14 (flexible strips not shown) is formed of a metastable hydrated salt and a reinforcing open micro-porous material. FIGS. 2A, 2B and 2C show various embodiments of the fill composition 14 within the outer covering 12. FIG. 2A shows a fill composition 14 formed of a metastable hydrated salt 16 and reinforcing hollowfill fibres 18 dispersed throughout the metastable salt 16. FIG. 2B shows a fill composition 14 comprising a bubble-pack plastics material 20. The bubble-pack material 20 is sandwiched between the two layers of the metastable hydrate compound 16 and the entire composition is enclosed within the outer covering 12.

FIG. 2C shows a further embodiment in which a hydrogel material 22 is dispersed throughout the metastable hydrated compound 16.

In use the metastable compound 16 is initially liquid. This allows the mouldable product to be moulded around the broken leg. The act of moulding the pad 10 flexes the strips 13 resulting in growth of the micro slits 16 which causes initiation of nucleation and results in the metastable compound 16 transforming to a solid and hence the product becomes rigid. Reinforcement of the rigid product is provided by way of the hollow fibre 18, the bubble-pack 20 or the hydrogel component 22 as shown in FIGS. 2A, 2B and 2C respectively.

In a modification the pad 10 incorporates metastable hydrated salt 16 formed of sodium acetate tri-hydrate with a small percentage of soluble starch, such as corn starch, homogeneously mixed therewith for the purpose of rendering the salt 16 comparatively viscous or gel like when the 'liquid' state. The level of viscosity is approximately proportional to the amount of starch employed so that by increasing the amount of starch the thickness of the salt increases correspondingly. The preferred viscosity is such as to make the salt 16 of lubrication-grease-like consistency. The starch acts like a thickening agent or gelling agent and may be replaced by alternatives such as cornflour, certain hydra-gels such as 'Watersorb', or Cellosize (RTM) made by Union Carbide. In addition to the salt 16 the fill composition 14 incorporates a sheet of cotton fibre gauze 18 which functions as the open micro-porous material, and a slit-metal trigger disc supplied by Prism Technologies Inc of San Antonio, Tex., USA which when manually manipulated from one of its bistable conditions to the other acts as the nucleating mechanism for the salt 16. The pad 10 incorporates a flexible plastic outer covering 12 which may be polyurethane, polythene or PVC typically of up to 500 μm in thickness. The covering 12 is welded along its periphery to provide a fluid tight environment for the salt 16 and additionally may be intermittently welded from back to front over its surface area to prevent 'bagging' or separation between the front and rear panels of the pad 10, and to provide a guilt like effect which reduces migration of the grease-like gel salt 16 under the influence of gravity since the interior of the pad 10 is effectively formed into packets or cells which are sufficiently interconnected to allow the salt 16 to be filled into the covering 12 from a single opening. By way of example the pad 10 is about 5 mm in thickness and when triggered transforms from pliable to rigid in about 10 minutes, releasing heat as it does so. It can subsequently be transformed from rigid to pliable by immersion in a water bath at a temperature of say 80° C. which is in excess of the freezing temperature (58° C.) of the salt 16. This reverse transformation takes about 15 minutes or so to ensure that all crystalline sites are melted away and do not remain as potential nucleation sites for initiating an unwanted pliable to rigid transformation. The exothermal pliable to rigid transformation may be incompatible for use directly against a patient's skin and therefore the pad 10 may be further encased in an insulating foam barrier housing externally-covered with a fabric (such as lycra) for aesthetic reasons.

By virtue of the present invention a mouldable product is provided which is conformable and is capable of being selectively converted from one substantially mouldable shape to another substantially rigid shape, the respective rigid shapes being defined by different users of the product.

We claim:

1. A mouldable product which is conformable in that it can be selectively converted from a mouldable state to a reinforced solid state and which in its mouldable state can be shaped or conformed to any desired configuration, said product comprising a sealed container made of permanently flexible material and a fill composition within said container, said composition comprising a reinforcing open micro-porous material which is liquid absorbing and a metastable compound dispersed through said micro-porous material and a triggering means for transforming said metastable compound to a solid state.

2. A mouldable product as claimed in claim 1, wherein the micro-porous material is a fibrous material.

3. A mouldable product as claimed in claim 2, wherein the fibrous micro-porous material incorporates cotton fibres.

4. A mouldable product as claimed in claim 1, wherein the micro-porous material is a particulate material.

5. A mouldable product as claimed in claim 1, wherein said triggering means is a flexible metal strip with micro slits cut in the surface of the strip.

6. A mouldable product as claimed in claim 1, wherein the metastable compound is a hydrated salt or mixture thereof.

7. A mouldable product as claimed in claim 6 wherein said hydrated salt is combined with a thickening or gelling agent to render said metastable compound of gel-like consistency.

8. A mouldable product as claimed in claim 1, wherein said mciro-porous material is a sheet of cotton gauze, said metastable compound is sodium acetate trihydrate in combination with starch to provide said metastable compound with lubrication-grease-like viscosity, and said container has front and rear panels of plastic film which are edge welded together and intermittently welded over the surface area to prevent separation between the front and rear panels and to form pockets or cells to reduce migration of the compound.

* * * * *